(12) United States Patent
Davis et al.

(10) Patent No.: US 11,619,613 B1
(45) Date of Patent: Apr. 4, 2023

(54) THERMOACOUSTIC MEASUREMENT PROBE

(71) Applicants: ENDRA Life Sciences Inc., Ann Arbor, MI (US); Duke University, Durham, NC (US)

(72) Inventors: Christopher Nelson Davis, Ann Arbor, MI (US); Paolo Maccarini, Durham, NC (US); Idan Steinberg, Superior Charter Township, MI (US); Michael M. Thornton, London (CA)

(73) Assignees: ENDRA Life Sciences Inc., Ann Arbor, MI (US); Duke University, Durham, NC (US)

( * ) Notice: Subject to any disclaimer, the term of this patent is extended or adjusted under 35 U.S.C. 154(b) by 0 days.

(21) Appl. No.: 17/946,700

(22) Filed: Sep. 16, 2022

(51) Int. Cl.
*G01N 29/24* (2006.01)
*H01P 11/00* (2006.01)

(52) U.S. Cl.
CPC ........ *G01N 29/2431* (2013.01); *H01P 11/002* (2013.01)

(58) Field of Classification Search
CPC ........... G01N 29/2431; G01N 29/2418; G01N 29/2437; G01N 29/24; G01N 29/2462; G01N 29/2443; H01P 11/002
See application file for complete search history.

(56) References Cited

U.S. PATENT DOCUMENTS

| | | | |
|---|---|---|---|
| 11,304,606 B2 * | 4/2022 | Davis | A61B 5/201 |
| 11,369,272 B1 * | 6/2022 | Davis | H01P 11/002 |
| 2013/0296683 A1 * | 11/2013 | Herzog | A61B 5/0095 600/407 |

* cited by examiner

*Primary Examiner* — Suman K Nath
(74) *Attorney, Agent, or Firm* — Stanley E. Jelic

(57) ABSTRACT

A thermoacoustic measurement probe may include an open-ended hollow radio-frequency (RF) waveguide; and a thermoacoustic transducer, wherein the open-ended hollow RF waveguide, in the form of a sleeve, surrounds and is mechanically joined to the thermoacoustic transducer.

20 Claims, 16 Drawing Sheets

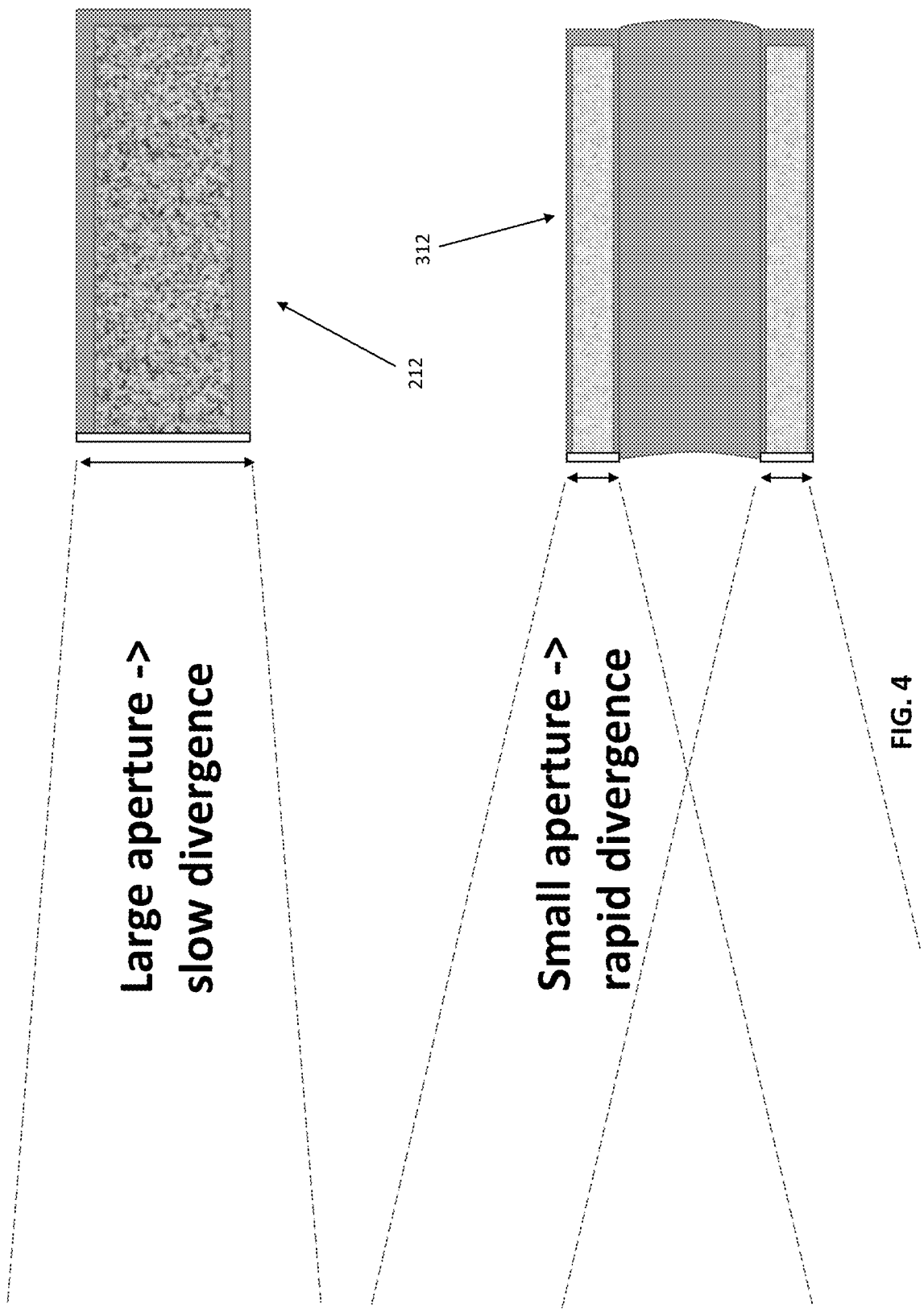

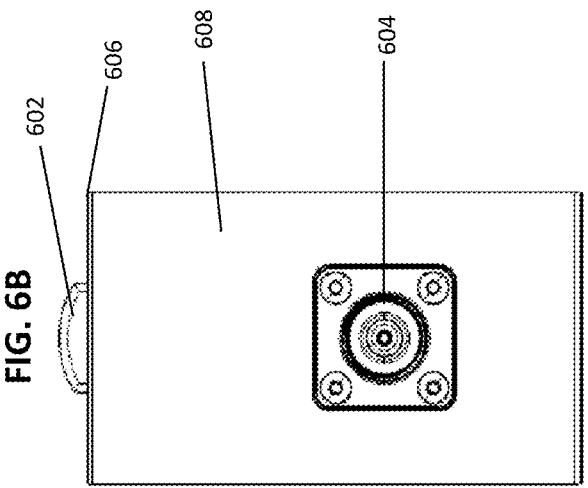
FIG. 6B
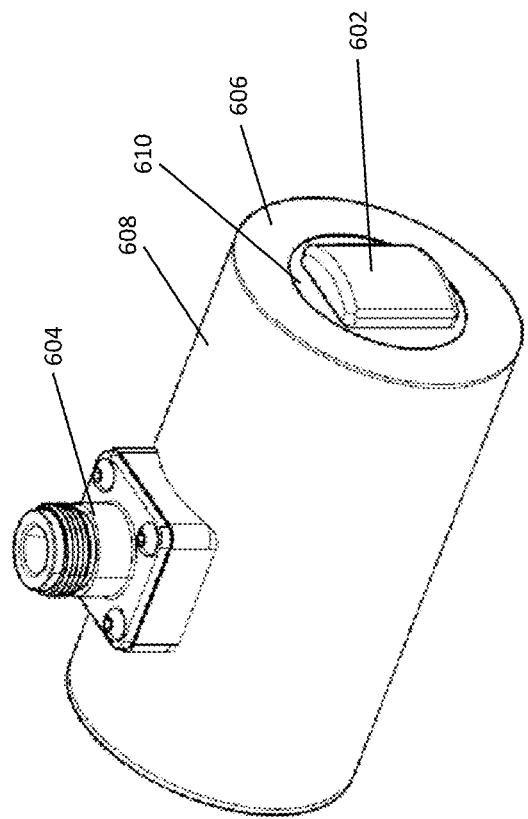
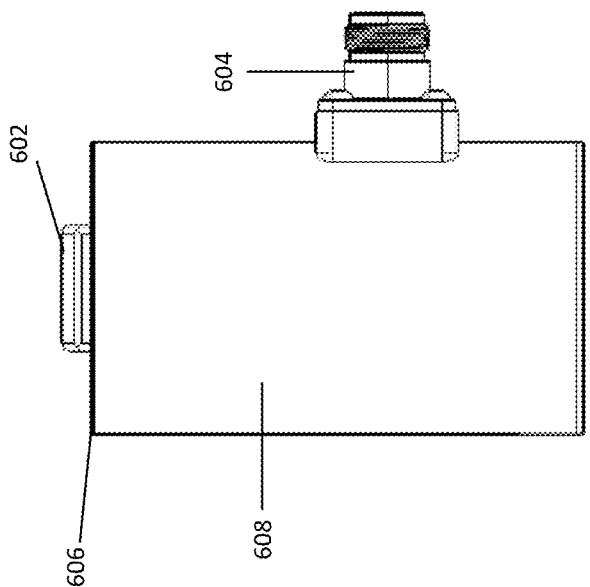
FIG. 6D
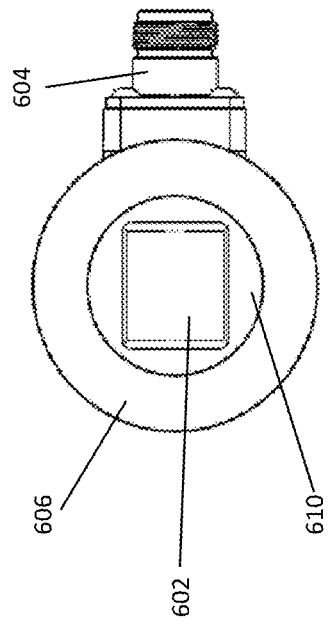
FIG. 6A
FIG. 6C

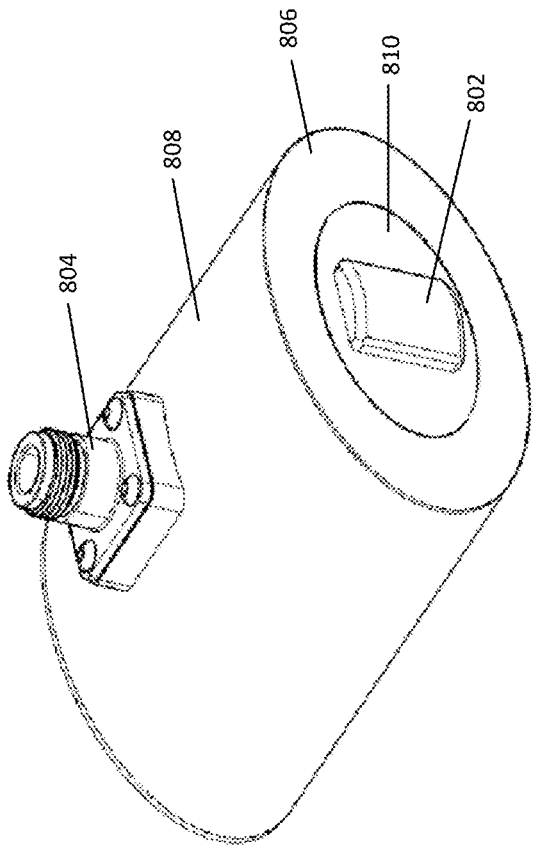
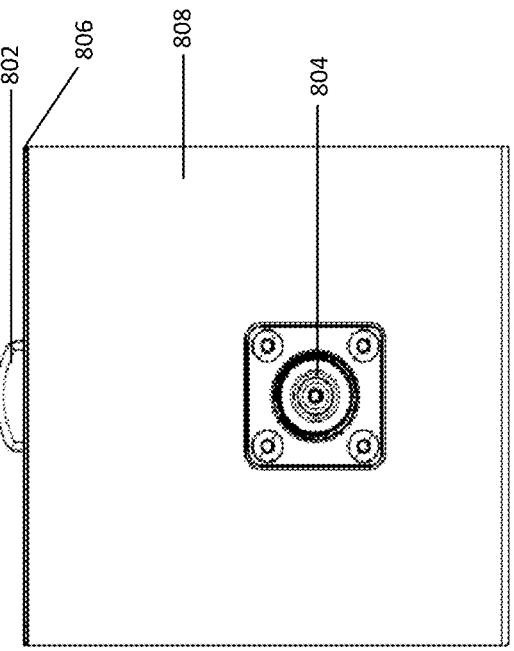
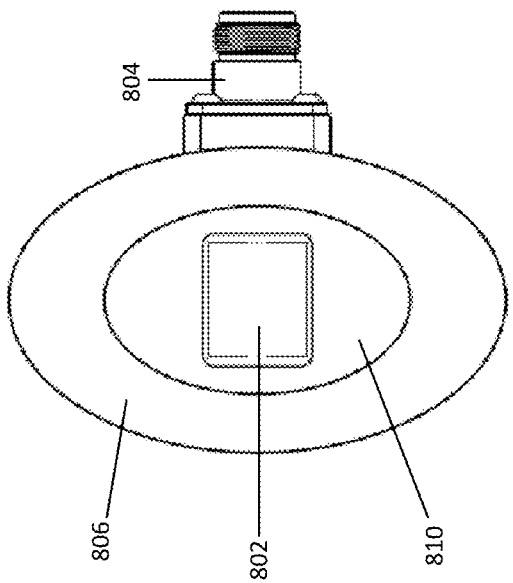
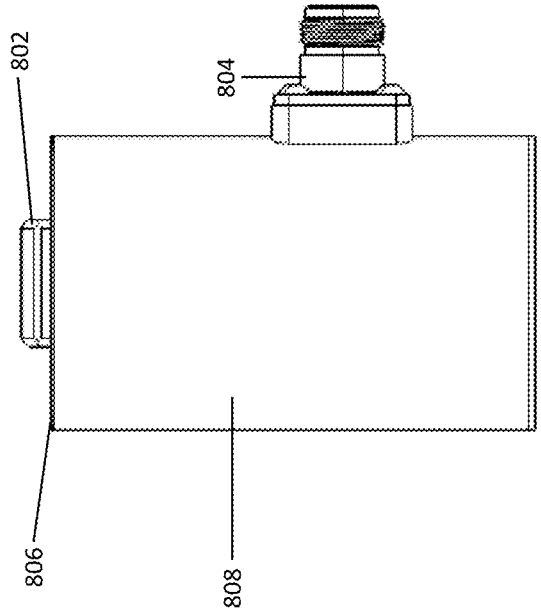
FIG. 8B
FIG. 8D
FIG. 8A
FIG. 8C

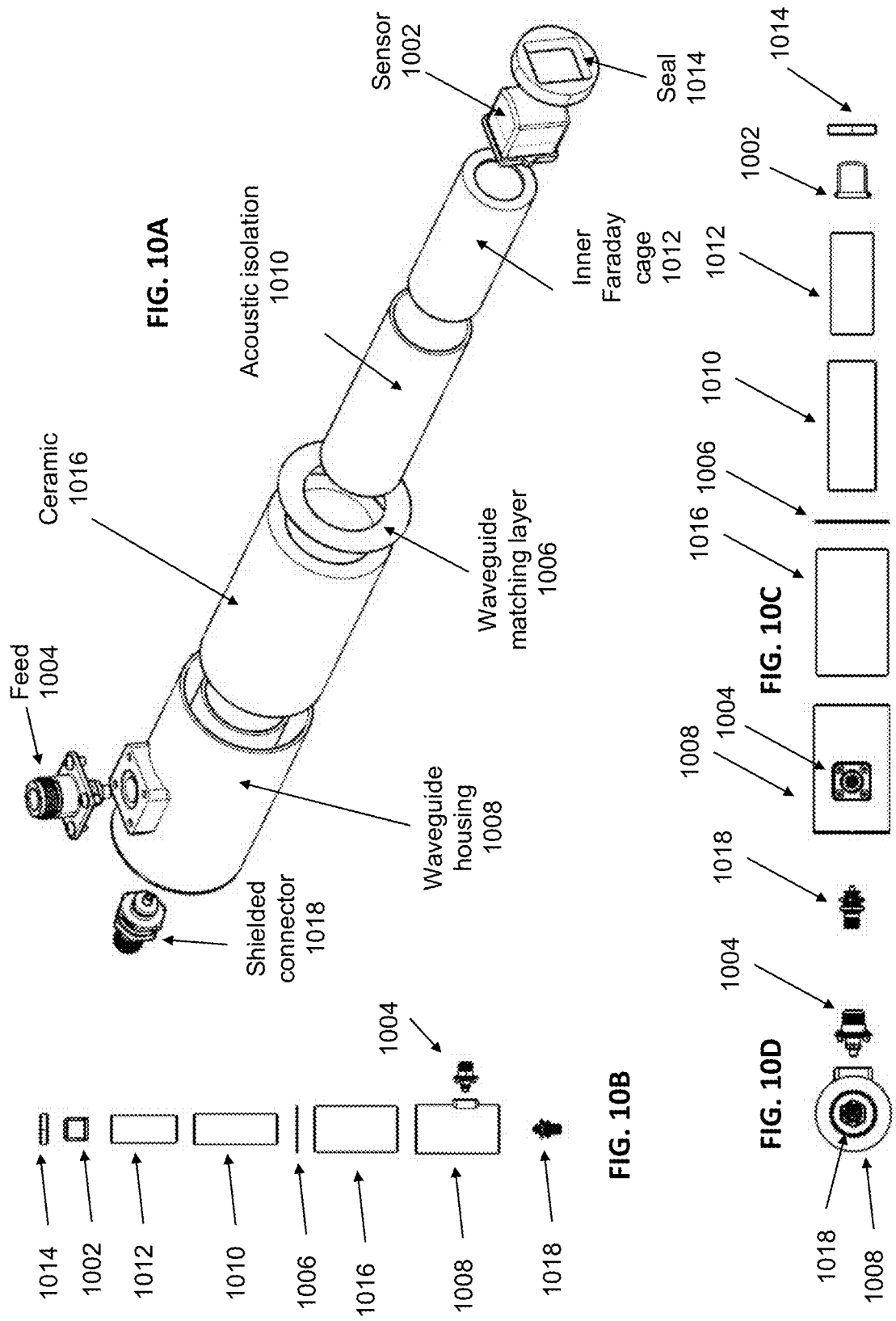

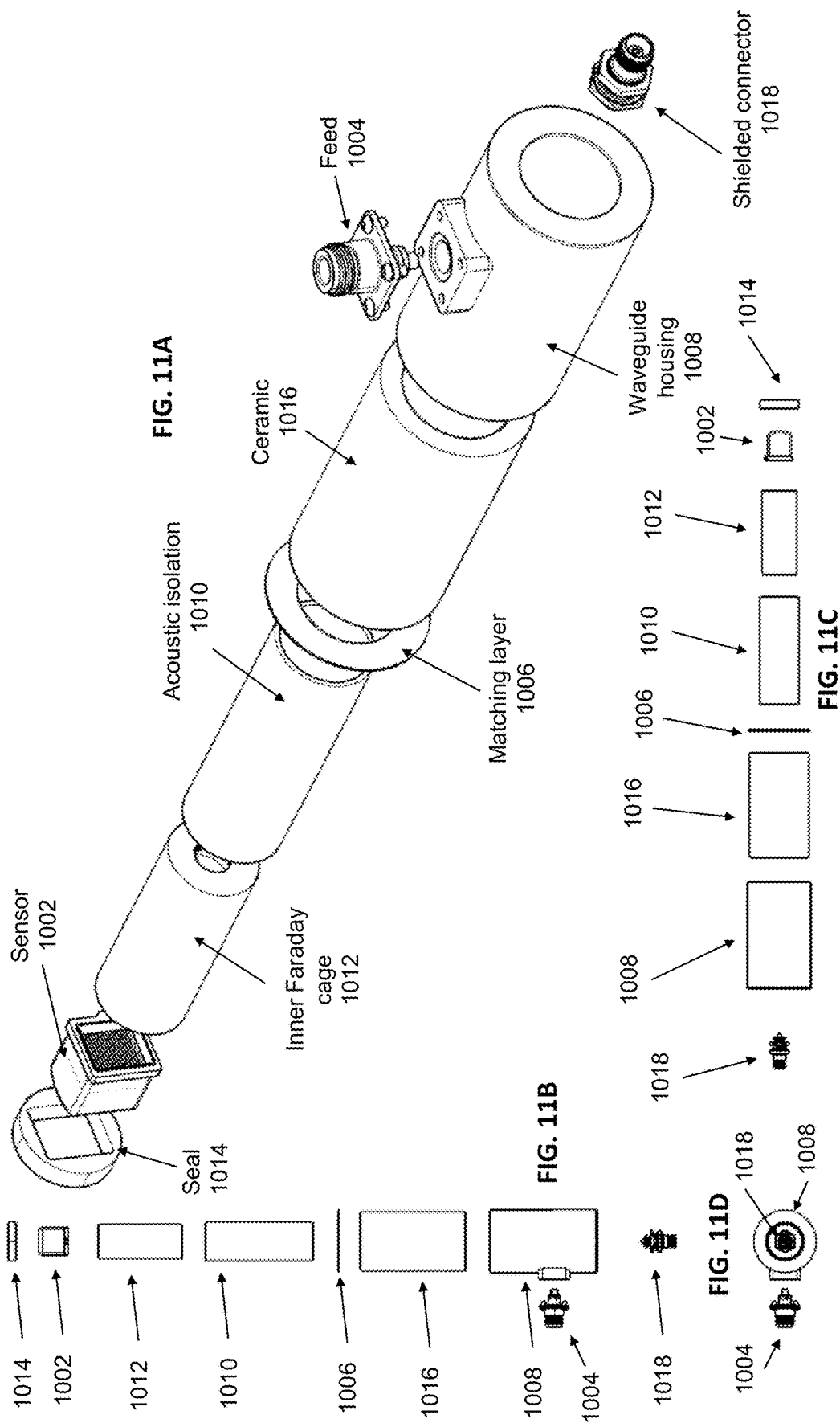

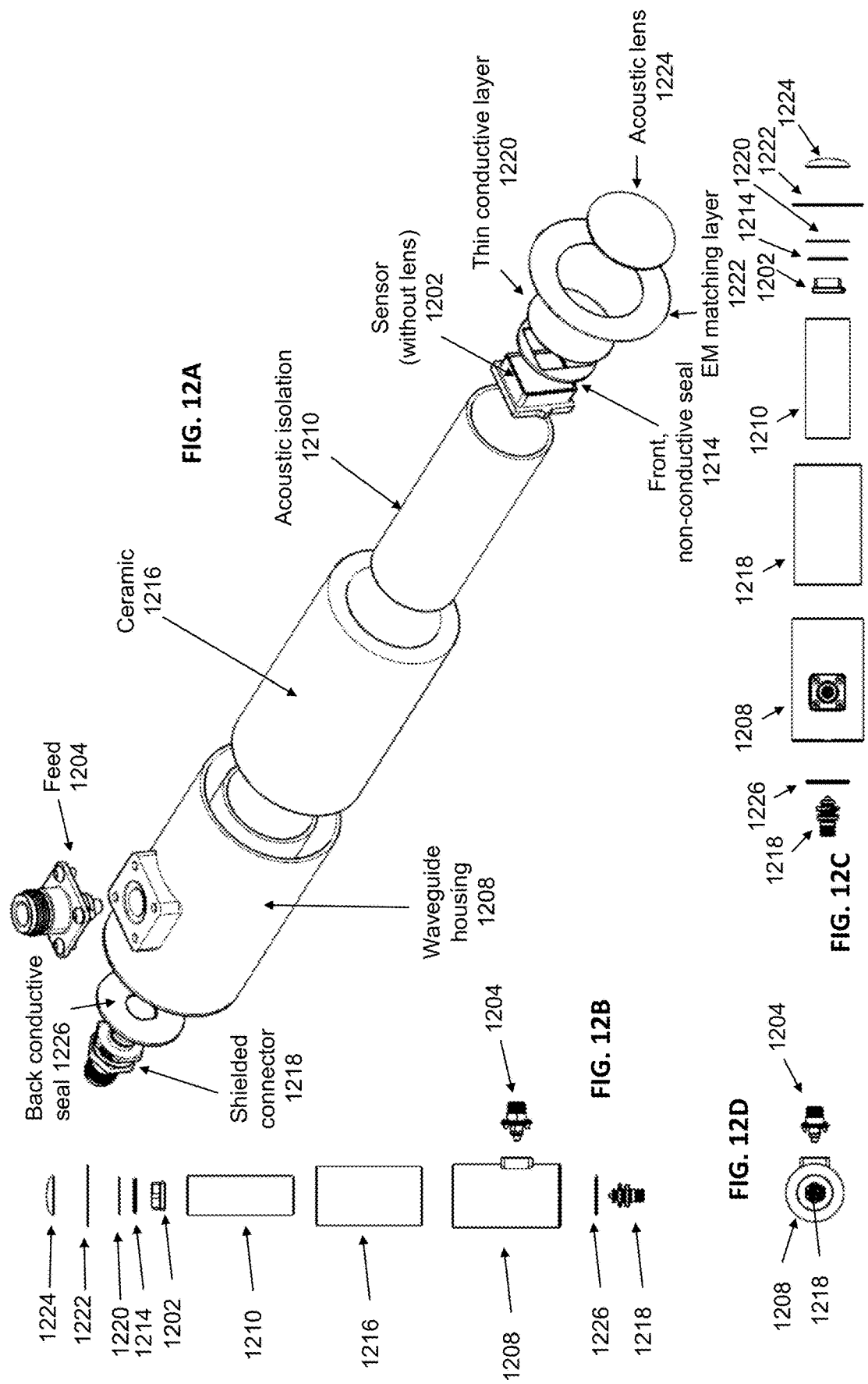

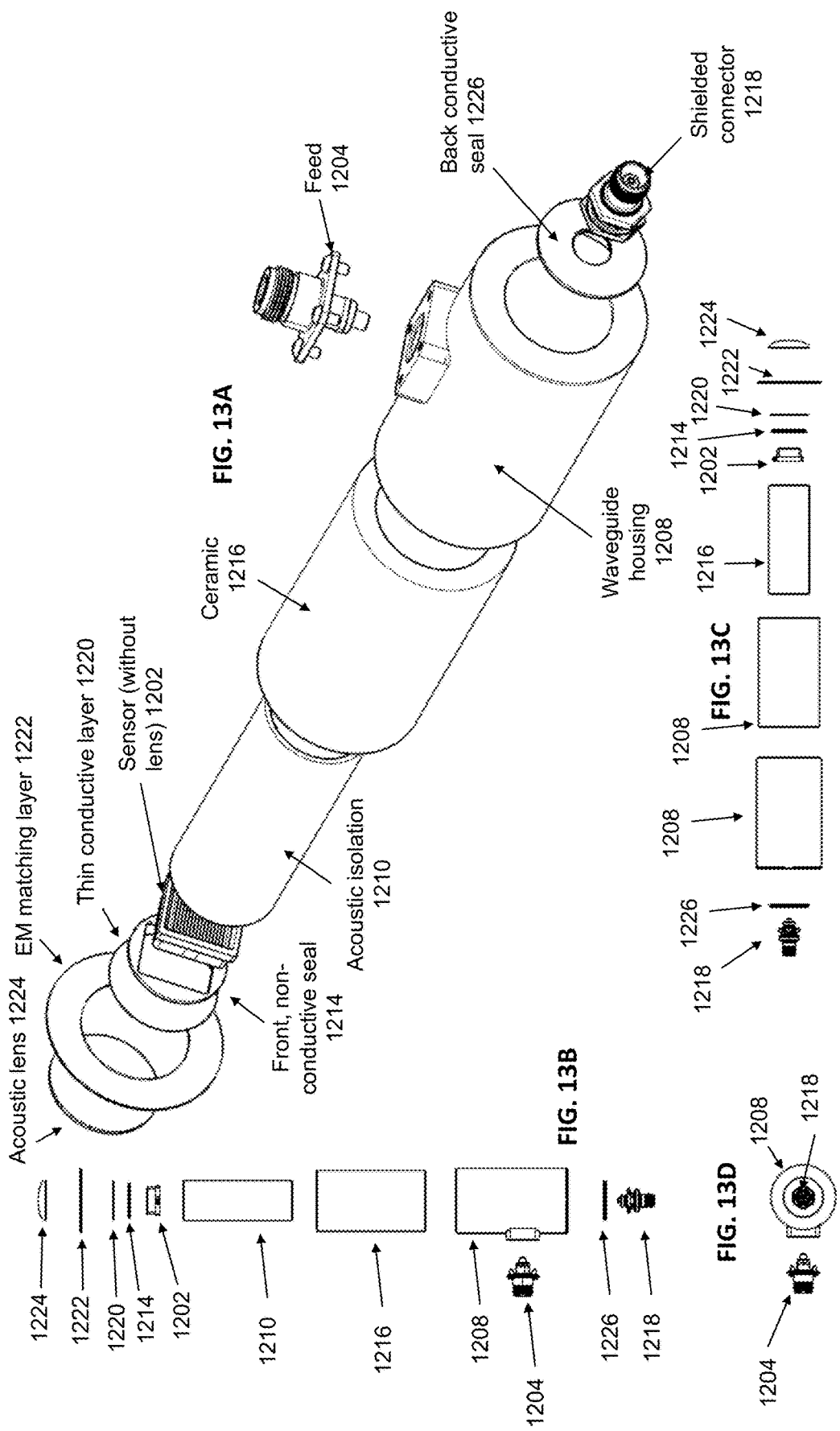

THERMOACOUSTIC MEASUREMENT PROBE

TECHNICAL FIELD

The present disclosure enables a thermoacoustic measurement probe. In particular, the disclosure discussed structural configurations that enable a radio-frequency (RF) waveguide portion of a probe to surround a thermoacoustic transducer portion.

BACKGROUND

In high frequency systems, it is common to employ waveguides to guide electromagnetic waves or sound with minimal loss of energy by restricting expansion of the electromagnetic waves propagating within the waveguides to one or two dimensions. Depending on the nature of the electromagnetic waves to be propagated, the waveguides may take different forms. Also, in many instances, filters are employed to allow electromagnetic waves at some frequencies to pass and travel along the waveguides, while rejecting electromagnetic waves at other frequencies. One example is hollow, open-ended conductive waveguides, which are often employed for directing radio frequency (RF) waves. In some instances, to provide the desired filtering these hollow metal waveguides are fitted with a solid insert formed of high dielectric constant material.

Waveguides such as those described above have been employed in thermoacoustic imaging systems. Thermoacoustic imaging is an imaging modality that provides information relating to the thermoelastic properties of tissue. Thermoacoustic imaging uses short pulses of electromagnetic energy, such as RF pulses, directed into a medium to heat absorbing features within the medium rapidly, which in turn induces acoustic pressure waves that are detected using acoustic receivers such as one or more thermoacoustic or ultrasound transducer arrays. The detected acoustic pressure waves are analyzed through signal processing, and processed for presentation as thermoacoustic images that an operator can interpret.

In order to direct RF pulses into the medium during thermoacoustic imaging, an RF applicator employing a waveguide is coupled to tissue adjacent to a region of interest (ROI) within the medium to be imaged. Sub-optimal coupling of the RF applicator to the tissue may cause issues such as inefficient energy transfer, reduced heating rates, reduced signal intensity, non-uniform energy deposition, tissue hotspots, tissue overheating, RF power supply damage, and poor image quality. Factors that lead to sub-optimal coupling of the RF applicator to the tissue include variability in the medium's size, the size of tissue within the medium, the geometry of tissue within the medium, the composition of tissue within the medium, etc.

In a thermoacoustic probe, an RF applicator or RF antenna are used for transmitting RF energy into the medium of interest, and an acoustic receiver is used to pick up the resulting thermoacoustic waves. It is common to configure the RF applicator and acoustic receiver side-by-side, integrated into a single handheld probe.

The side-by-side configuration may result in lower thermoacoustic signal strength, thereby reducing the effectiveness of thermoacoustic measurements. This is because the signal strength and extent of the imageable region are dependent on the extent of overlap between the RF applicator beam and the acoustic receiver's directivity pattern.

Another disadvantage of a side-by-side configuration for a thermoacoustic probe is that RF interference from the RF applicator may also adversely affect signal quality.

A third disadvantage of a side-by-side configuration for a thermoacoustic probe may be that spurious acoustic signals, such as an RF applicator plane wave, are stronger and are detrimental to acoustic signal fidelity.

In a side-by-side configuration, one proposed solution is to tilt the acoustic receiver in relation to RF applicator. This approach can allow for better overlap, but only a certain depth. Unfortunately, this will not improve RFI or reduce a large plane-wave artifact (unwanted signal noise) that occurs.

Another proposed solution is to separate the receiver and applicator into two different devices that can increase signal strength and reduce artifacts. Unfortunately, this approach introduces multiple complications and higher variability, as now an operator needs to manipulate two devices simultaneously, which represents a massive obstruction to the standard of care clinical workflow.

Hence, there is a need to develop a novel structural thermoacoustic probe configuration that overcomes the limitations inherent in a side-by-side thermoacoustic probe configuration.

SUMMARY

In one embodiment, a thermoacoustic measurement probe may comprise an open-ended hollow RF waveguide and a thermoacoustic transducer, wherein the open-ended hollow RF waveguide, in the form of a sleeve, surrounds and is mechanically joined to the thermoacoustic transducer.

The open-ended hollow RF waveguide, in the form of a sleeve, may surrounds and be mechanically joined to the thermoacoustic transducer via insulation that protects the thermoacoustic transducer from acoustic and electrical interference emanating from the open-ended hollow RF waveguide.

The thermoacoustic transducer and open-ended hollow RF waveguide may form a circular cross-sectional shape.

The thermoacoustic transducer and open-ended hollow RF waveguide may form an elliptical cross-sectional shape.

A sensor of the thermoacoustic transducer may have a circular cross-sectional shape.

A sensor of the thermoacoustic transducer may have an elliptical cross-sectional shape.

A sensor of the thermoacoustic transducer may have a rectangular cross-sectional shape.

An end of a sensor of the thermoacoustic transducer may have a conical shape.

In another embodiment, a thermoacoustic measurement probe may comprise a radio-frequency (RF) waveguide having a cavity and a thermoacoustic transducer positioned in the cavity of the RF waveguide.

The cavity of the RF waveguide may have a circular cross-sectional shape.

The cavity of the RF waveguide may have an elliptical cross-sectional shape.

The cavity of the RF waveguide may have a rectangular cross-sectional shape.

A sensor of the thermoacoustic transducer may have a circular cross-sectional shape.

A sensor of the thermoacoustic transducer may have an elliptical cross-sectional shape.

A sensor of the thermoacoustic transducer may have a rectangular cross-sectional shape.

A sensor of the thermoacoustic transducer may have a conical shape.

A ceramic may be positioned in the cavity.

An acoustic isolation may be positioned in the ceramic.

The thermoacoustic measurement probe may comprise an RF feed coupled to the RF waveguide, and a connector coupled to the thermoacoustic transducer via an opening in the RF waveguide.

In yet another embodiment, a thermoacoustic measurement probe may comprise a cylindrical radio-frequency (RF) waveguide housing; a cylindrical ceramic inside the cylindrical RF waveguide housing; a cylindrical acoustic isolation inside of the cylindrical ceramic; and a thermoacoustic sensor at an end of the cylindrical acoustic isolation.

It should be appreciated that this summary is provided to introduce a selection of concepts in a simplified form that are further described below in the detailed description. This summary is not intended to be used to limit the scope of the claimed subject matter.

BRIEF DESCRIPTION OF THE DRAWINGS

Embodiments will now be described more fully with reference to the accompanying drawings in which:

FIG. 4 is a signal divergence comparison between a standard RF applicator used in the prior art and the sleeve RF applicator of the present application.

FIG. 6A is a front view of a second RF applicator and acoustic receiver sleeve configuration, according to an embodiment.

FIG. 6B is a perspective view of the second RF applicator and acoustic receiver sleeve configuration, according to an embodiment.

FIG. 6C is a side view of the second RF applicator and acoustic receiver sleeve configuration, according to an embodiment.

FIG. 6D is a top view of the second applicator and acoustic receiver sleeve configuration, according to an embodiment.

FIG. 8A is a front view of a fourth RF applicator and acoustic receiver sleeve configuration, according to an embodiment.

FIG. 8B is a perspective view of the fourth RF applicator and acoustic receiver sleeve configuration, according to an embodiment.

FIG. 8C is a side view of the fourth RF applicator and acoustic receiver sleeve configuration, according to an embodiment.

FIG. 8D is a top view of the fourth applicator and acoustic receiver sleeve configuration, according to an embodiment.

FIG. 10A is an exploded isometric view of a sixth RF applicator and acoustic receiver sleeve configuration, according to an embodiment.

FIG. 10B is an exploded side view of the sixth RF applicator and acoustic receiver sleeve configuration, according to an embodiment.

FIG. 10C is an exploded top view of the sixth RF applicator and acoustic receiver sleeve configuration, according to an embodiment.

FIG. 10D is an exploded side view of the sixth RF applicator and acoustic receiver sleeve configuration, according to an embodiment.

FIG. 11A is an alternative exploded isometric view of the sixth RF applicator and acoustic receiver sleeve configuration, according to an embodiment.

FIG. 11B is an alternative exploded side view of the sixth RF applicator and acoustic receiver sleeve configuration, according to an embodiment.

FIG. 11C is an alternative exploded top view of the sixth RF applicator and acoustic receiver sleeve configuration, according to an embodiment.

FIG. 11D is an alternative exploded side view of the sixth RF applicator and acoustic receiver sleeve configuration, according to an embodiment.

FIG. 12A is an exploded isometric view of a seventh RF applicator and acoustic receiver sleeve configuration, according to an embodiment.

FIG. 12B is an exploded side view of the seventh RF applicator and acoustic receiver sleeve configuration, according to an embodiment.

FIG. 12C is an exploded top view of the seventh RF applicator and acoustic receiver sleeve configuration, according to an embodiment.

FIG. 12D is an exploded side view of the seventh RF applicator and acoustic receiver sleeve configuration, according to an embodiment.

FIG. 13A is an alternative exploded isometric view of the seventh RF applicator and acoustic receiver sleeve configuration, according to an embodiment.

FIG. 13B is an alternative exploded side view of the seventh RF applicator and acoustic receiver sleeve configuration, according to an embodiment.

FIG. 13C is an alternative exploded top view of the seventh RF applicator and acoustic receiver sleeve configuration, according to an embodiment.

FIG. 13D is an alternative exploded side view of the seventh RF applicator and acoustic receiver sleeve configuration, according to an embodiment.

DETAILED DESCRIPTION

Embodiments herein describe a thermoacoustic measurement probe having an RF waveguide that surrounds a thermoacoustic transducer, and a housing of the thermoacoustic measurement probe contains both the RF waveguide and the thermoacoustic transducer.

Embodiments herein describe an improved method and system. Rather than utilizing an open-ended RF waveguide and a separate acoustic receiver, the embodiments discussed herein may utilize an open-ended hollow RF waveguide, wherein the hollow portion is a cavity configured for an acoustic receiver and any additional electronics to be mounted within that cavity. This configuration may allow the mechanical installation of the acoustic receiver (thermoacoustic transducer) and any additional electronics inside the hollow cavity. The open-ended RF waveguide may be configured in a form of a sleeve, which may partially or entirely surround the acoustic receiver. The RF waveguide may also be mechanically joined to the acoustic receiver.

The use of a hollow RF waveguide is not conventionally used with a component, such as a thermoacoustic transducer, in a hollow portion, because a component could affect the field and operation of the RF waveguide. In the embodiments described herein, the RF waveguide may be configured with a null region in the hollow portion.

An unexpected result of placing the acoustic receiver inside the hollow cavity of an open-ended hollow RF waveguide is that it allows for maximal overlap between the RF beam and the acoustic receiver's directivity pattern.

Another unexpected result of utilizing an open-ended hollow RF waveguide is a very low electromagnetic field inside the hollow cavity. Placing the acoustic receiver inside the cavity (within the sleeve) reduces RF interferences significantly.

Another unexpected result is that the hollow RF waveguide has a highly divergent beam pattern near the RF waveguide. This, in turn, generates a diverging applicator plane wave which quickly disperses.

An unexpected result is that the hollow RF waveguide allows for smaller overall thermoacoustic measurement probe dimensions because the electronics and acoustic receiver can be placed inside the hollow cavity.

The cross-sectional shape of the hollow portion of the open-ended hollow RF waveguide can be any shape, including circular, elliptical, non-concentric tube, or tapered tube. The open-ended portion may contain a ceramic fill. In one embodiment, metal fins may be included in the ceramic fill or mounted on the RF waveguide to increase the frequency bandwidth over which the RF applicator can efficiently operate.

Figure 1:
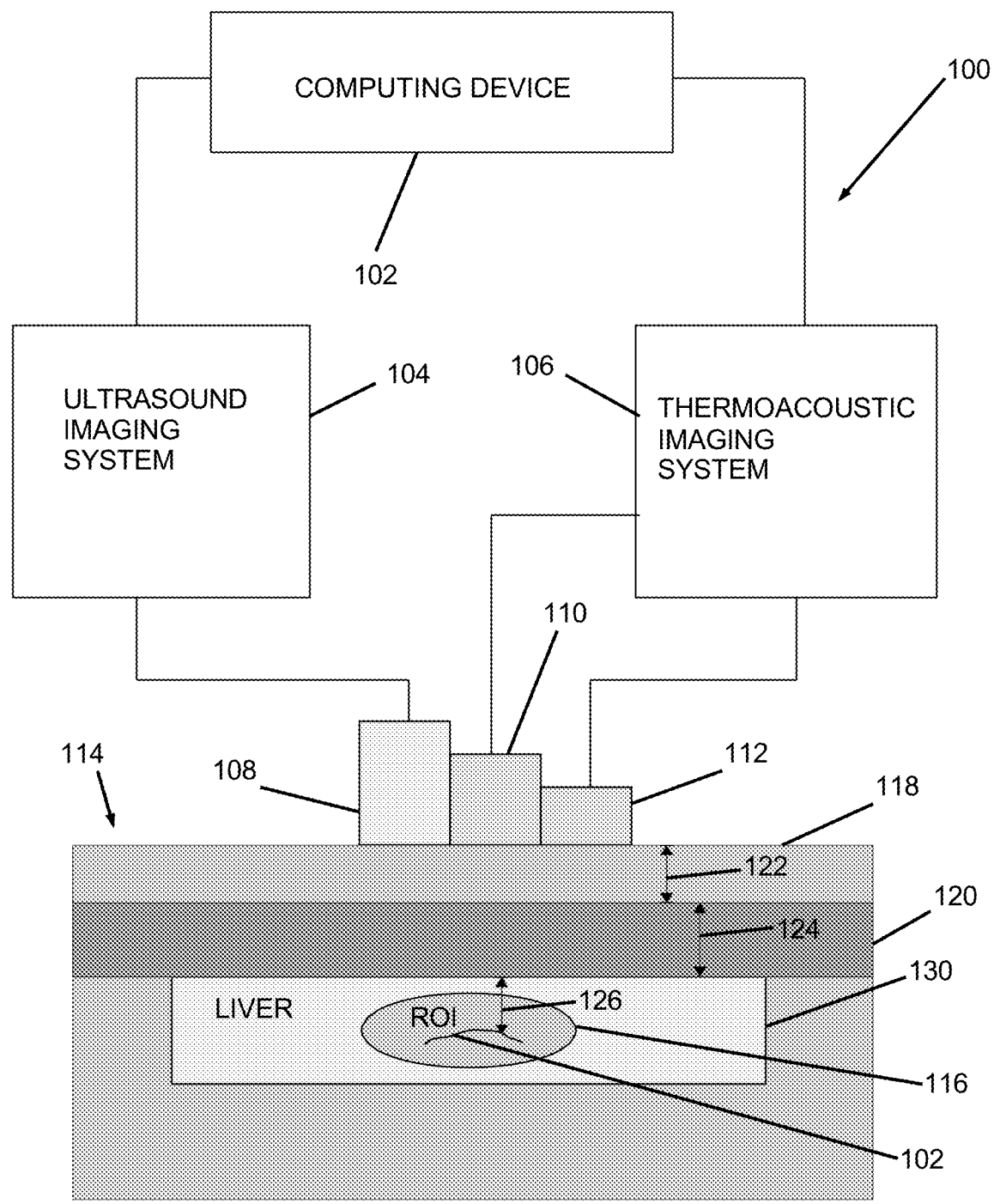
FIG. 1 is a block diagram of a thermoacoustic system, according to an embodiment.

Turning now to FIG. 1, an imaging system is shown and is generally identified by reference numeral 100. As can be seen, the imaging system 100 comprises a programmed computing device 102 communicatively coupled to an ultrasound imaging system 104 and to a thermoacoustic imaging system 106. The ultrasound imaging system 104 and thermoacoustic imaging system 106 are configured to obtain ultrasound image data and thermoacoustic image data, respectively, of a region of interest (ROI) 116.

The programmed computing device 102 in this embodiment may be a personal computer, server, or other suitable processing device comprising, for example, a processing unit comprising one or more processors, computer-readable system memory (volatile and/or non-volatile memory), other non-removable or removable computer-readable memory (e.g., a hard disk drive, RAM, ROM, EEPROM, CD-ROM, DVD, flash memory, etc.) and a system bus coupling the various computer components to the processing unit. The computing device 102 may also comprise networking capabilities using Ethernet, Wi-Fi, and/or another suitable network format to enable connection to shared or remote drives, one or more networked computers, or other networked devices. One or more input devices, such as a mouse and a keyboard (not shown) are coupled to the computing device 102 for receiving operator input. A display device (not shown), such as one or more computer screens or monitors, may be coupled to the computing device 102 for displaying one or more generated images that are based on ultrasound image data received from the ultrasound imaging system 104 and/or the thermoacoustic image data received from the thermoacoustic imaging system 106. The programmed computing device 102 executes program code stored on the computer-readable system memory and/or other non-removable or removable computer-readable memory and performs methods according to the program code, as described further below.

The ultrasound imaging system 104 comprises an acoustic receiver in the form of an ultrasound transducer 108 that houses one or more ultrasound transducer arrays configured to emit sound waves into the region of interest 116. Sound waves directed into the region of interest 116 echo off materials within the region of interest, with different materials reflecting varying degrees of sound. Echoes that are received by the one or more ultrasound transducer arrays of the ultrasound transducer 108 are processed by the ultrasound imaging system 104. The ultrasound imaging system 104 communicates ultrasound image data to the computing device 102 for further processing and for presentation on the display device as ultrasound images that an operator can interpret. In one embodiment, the ultrasound imaging system 104 utilizes B-mode ultrasound imaging techniques assuming a nominal speed of sound of 1,540 m/s. As ultrasound imaging systems are known in the art, further specifics of the ultrasound imaging system 104 will not be described further herein.

The thermoacoustic imaging system 106 comprises an acoustic receiver in the form of a thermoacoustic transducer 110. The thermoacoustic transducer 110 houses one or more thermoacoustic transducer arrays. As described herein, although shown as separate components in the schematic FIG. 1, a radio-frequency (RF) applicator (or waveguide) 112 may be housed, combined, or integrated with the thermoacoustic transducer 110. The RF applicator 112 is configured to emit short pulses of RF energy that are directed into the region of interest 116. In one embodiment, the RF applicator 112 has a frequency between about 10 Mhz and 100 GHz and has a pulse duration between about 0.1 nanoseconds and 10 microseconds. The RF applicator 112 emits RF energy pulses to materials or tissue within the region of interest 116 to induce acoustic pressure waves (thermoacoustic multi-polar signals) within the region of interest 116 that are detected by the thermoacoustic transducer 110. Acoustic pressure waves detected by the thermoacoustic transducer 110 are processed and communicated as thermoacoustic image data to the computing device 102 for further processing and presentation on the display device as thermoacoustic images that the operator can interpret.

The coordinate system of the one or more ultrasound transducer arrays of the ultrasound transducer 108 and the coordinate system of the one or more thermoacoustic transducer arrays of the thermoacoustic transducer 110 are mapped by the computing device 102 so that acquired ultrasound and thermoacoustic images can be registered. Alternatively, the thermoacoustic imaging system 106 may make use of the one or more ultrasound transducer arrays of the ultrasound transducer 108 by disconnecting the one or more ultrasound transducer arrays from the ultrasound transducer 108 and connecting the one or more ultrasound transducer arrays to the thermoacoustic transducer 110. As will be appreciated, by doing this coordinate mapping between the one or more ultrasound transducer arrays and the one or more thermoacoustic transducer arrays is not required.

In one embodiment (shown in FIG. 1), the region of interest 116 contains blood vessel 102 and is located within a liver 130 of a human or animal body (patient) 114. Patient 114 comprises a subcutaneous fat layer 118 and muscle layer 120 adjacent to liver 130. Distances shown: $d_f$ is the subcutaneous fat thickness of the patient 122, $d_m$ is the muscle thickness of the patient 124, $d_b$ is the distance from the boundary between the muscle and the liver to the center of the blood vessel 126.

Figure 2:
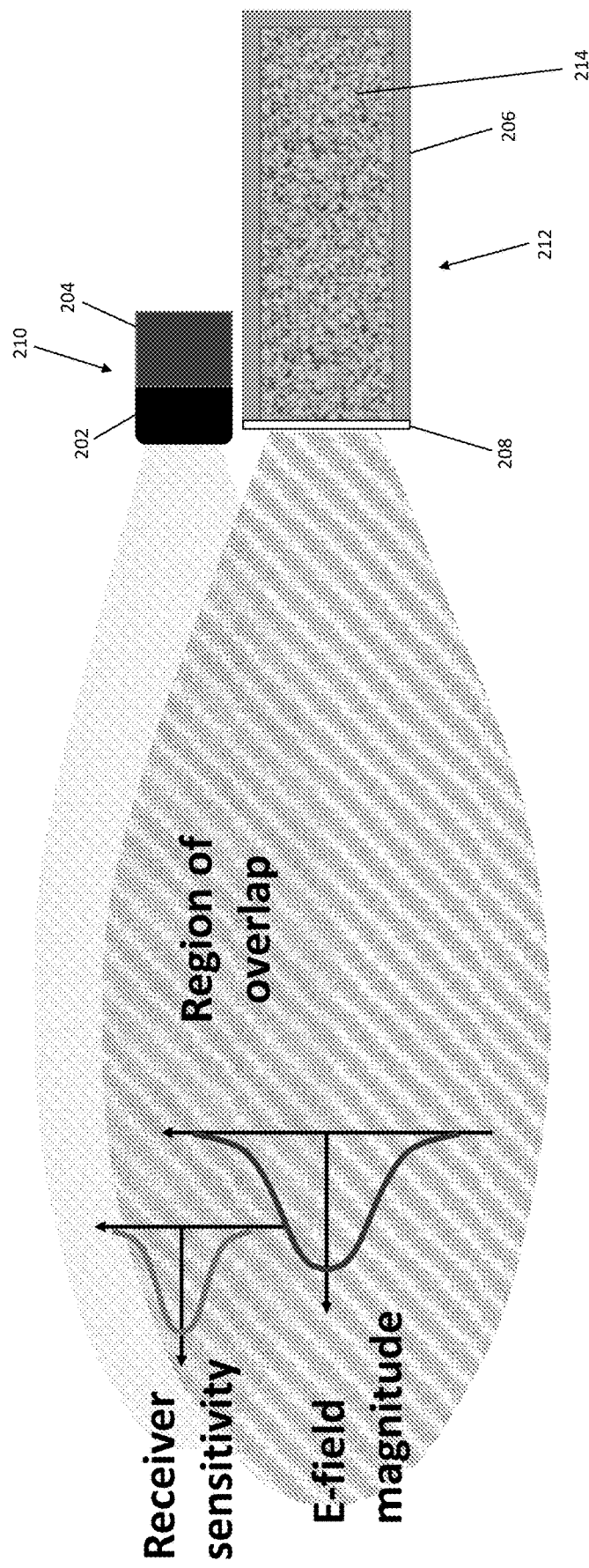
FIG. 2 is a cross-sectional side-view of an RF applicator and acoustic receiver side-by-side configuration, according to an embodiment.

FIG. 2 is a cross-sectional side-view of an RF applicator and acoustic receiver side-by-side configuration embodiment. Shown are thermoacoustic transducer 210 including thermoacoustic sensor 202 and thermoacoustic electronics 204, and RF applicator 212 including RF waveguide 206, RF matching layer 208, and RF applicator fill 214. In the side-by-side configuration of FIG. 2, an area/volume of an electric field with sufficient magnitude to generate a thermoacoustic signal and the area/volume of receiver sensitivity to detect and utilize a thermoacoustic signal have a small region of overlap. Hence, a thermoacoustic analysis occurs within this small region of overlap.

Figure 3:
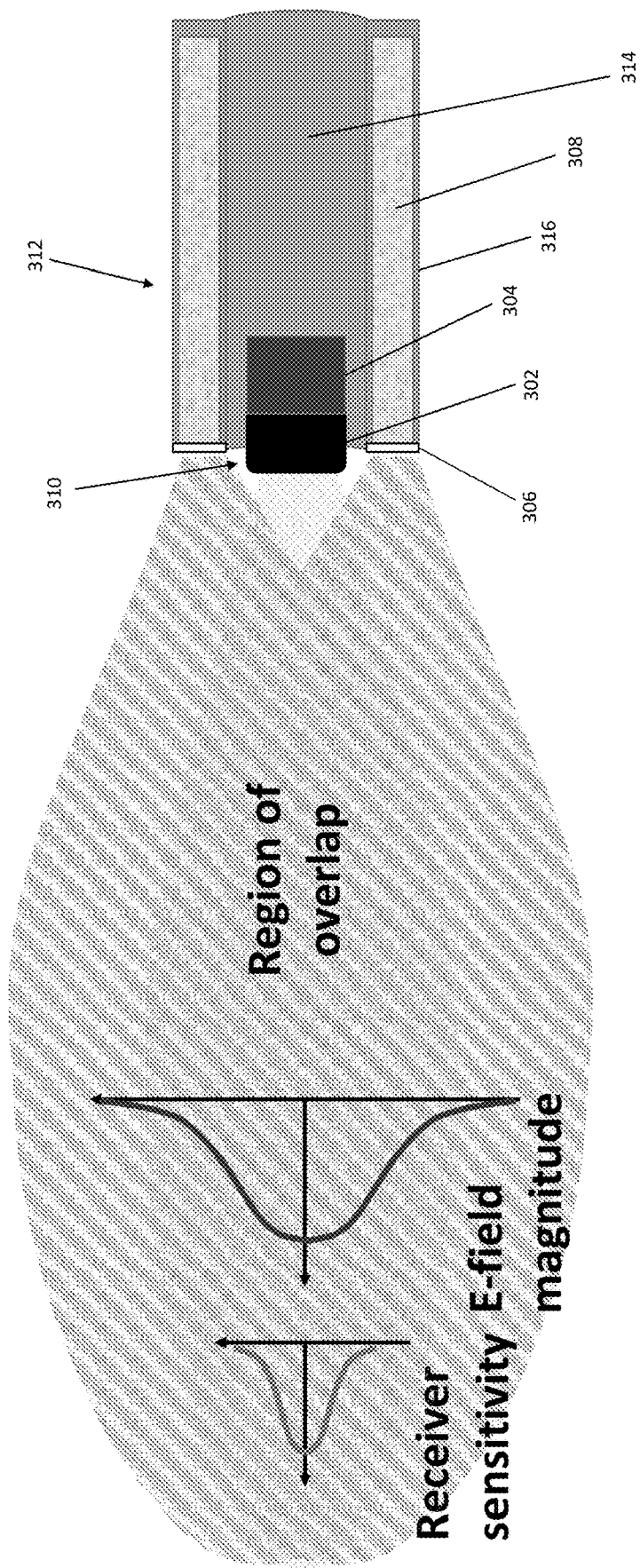
FIG. 3 is a cross-sectional side-view of an RF applicator and acoustic receiver sleeve configuration, according to an embodiment.

The thermoacoustic transducer may be configured to be housed within a cavity formed by the RF applicator. In one example, FIG. 3 is a cross-sectional side-view of an RF applicator and acoustic receiver configuration. Shown are open-ended hollow RF applicator 312, open-ended hollow waveguide body 316, open-ended hollow waveguide matching layer 306, open-ended hollow waveguide fill 308, thermoacoustic transducer 310, thermoacoustic sensor 302, thermoacoustic electronics 304, and insulation 314 (providing both acoustic and electromagnetic insulation). In this embodiment, the thermoacoustic transducer 310 is positioned within an interior region of the open-ended hollow RF applicator 312. In this configuration of FIG. 3, an area/volume of an electric field with sufficient magnitude to generate a thermoacoustic signal and the area/volume of receiver sensitivity to detect and utilize a thermoacoustic signal have a larger region of overlap as compared to FIG. 2.

FIG. 4 illustrates a signal divergence comparison between a conventional RF applicator shown in FIG. 2 and the RF applicator configuration shown in FIG. 3. RF applicator 212 is shown as a solid RF applicator with a large aperture and a slow divergence of RF energy. Open-ended hollow RF applicator 312 is shown with a small aperture where the RF energy is emitted and rapid divergence of RF energy. The divergence of RF energy is inversely proportional to the antenna aperture: the smaller the aperture, the larger the divergence angle, and vice versa. As shown in FIG. 4, the open-ended hollow RF applicator 312 has a smaller aperture, and this produces a larger divergence of the RF energy from the radiating surface of the applicator.

Figure 5B:
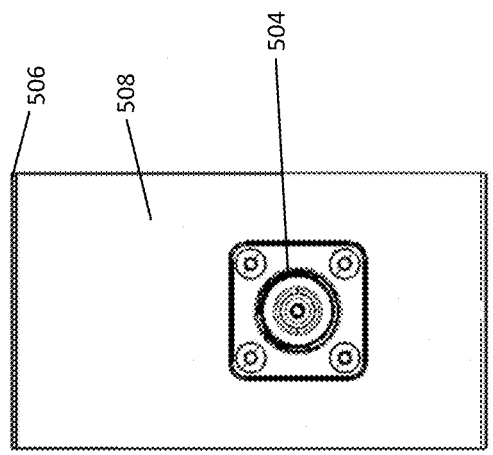
FIG. 5B is a perspective view of the first RF applicator and acoustic receiver sleeve configuration, according to an embodiment.
Figure 5D:
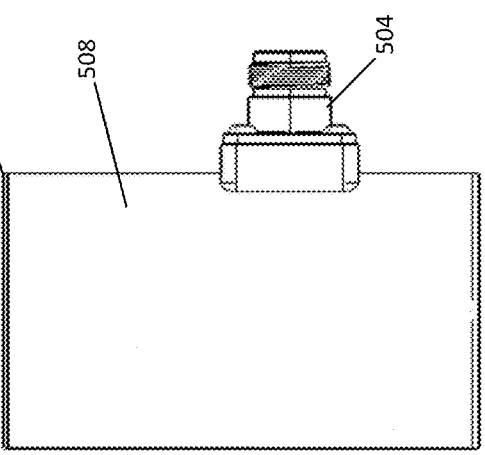
FIG. 5D is a top view of the first applicator and acoustic receiver sleeve configuration, according to an embodiment.
Figure 5A:
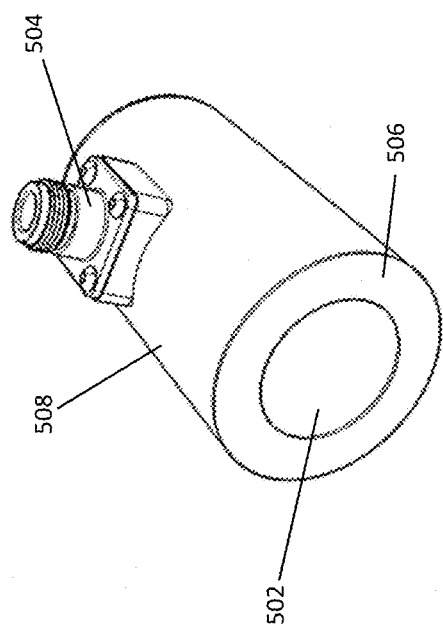
FIG. 5A is a front view of a first RF applicator and acoustic receiver sleeve configuration, according to an embodiment.
Figure 5C:
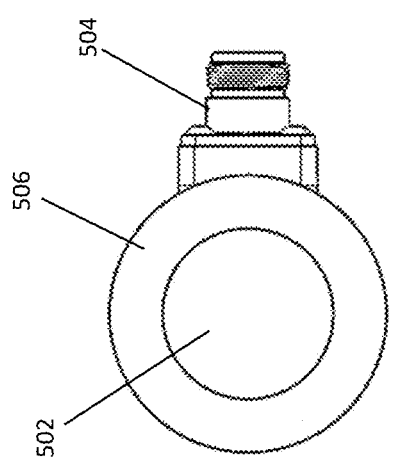
FIG. 5C is a side view of the first RF applicator and acoustic receiver sleeve configuration, according to an embodiment.

FIGS. 5A to 5D illustrate an RF applicator according to an embodiment. FIG. 5A is a front view of an RF applicator and acoustic receiver sleeve configuration embodiment. FIG. 5B is a perspective view of the RF applicator and acoustic receiver sleeve configuration embodiment. Shown are hollow cavity 502, open-ended hollow waveguide matching layer 506, open-ended hollow waveguide body 508, and RF energy feed 504. FIG. 5C is a side view of the RF applicator and acoustic receiver sleeve configuration embodiment. FIG. 5D is a top view of the applicator and acoustic receiver sleeve configuration embodiment. In the illustrations of FIGS. 5A to 5D, the hollow cavity 502 is configured to receive an acoustic receiver (thermoacoustic transducer). The RF applicator may be considered an acoustic receiver sleeve because it is at least partially hollow and configured to house the acoustic receiver (not shown) in that opening. The acoustic receiver may fill all or a portion of the hollow cavity 502, and any portion of the hollow cavity 502 not filled by the acoustic receiver may be at least partially filled by another material, such as insulation.

As shown in examples of FIGS. 5A to 9D, an RF applicator and an acoustic receiver may have different shapes and configures. The RF applicator may be circular, elliptical, or other configuration having an open-ended portion (e.g., cavity) for receiving the acoustic receiver. The acoustic receiver may have a rectangular, circular, elliptical, or other shape cross-section, and may have a rectangular, spherical, conical, or other shape end. FIGS. 5A to 9D are meant to be examples of configurations and the potential configurations are not limited to these particular examples. The shape may be selected based on the desired application or manufacturing processes.

In one configuration, the acoustic receiver may have a rectangular shape and be positioned in an RF applicator, as shown in FIGS. 6A to 6D. FIG. 6A is a front view of a second RF applicator and acoustic receiver sleeve configuration embodiment. FIG. 6B is a perspective view of a second RF applicator and acoustic receiver sleeve configuration embodiment. Shown are open-ended hollow waveguide matching layer 606, open-ended hollow waveguide body 608, RF energy feed 604, insulation 610, and rectangular acoustic receiver 602 (with rectangular cross-section). FIG. 6C is a side view of a second RF applicator and acoustic receiver sleeve configuration embodiment. FIG. 6D is a top view of a second applicator and acoustic receiver sleeve configuration embodiment.

Figure 7B:
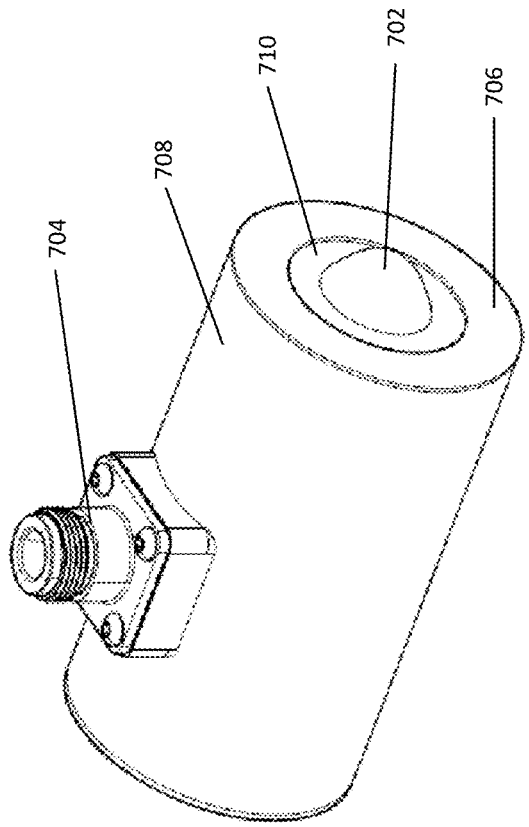
FIG. 7B is a perspective view of the third RF applicator and acoustic receiver sleeve configuration, according to an embodiment.
Figure 7D:
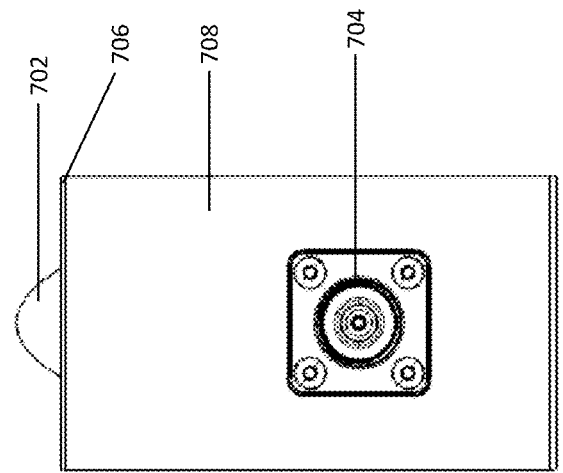
FIG. 7D is a top view of the third applicator and acoustic receiver sleeve configuration, according to an embodiment.
Figure 7A:
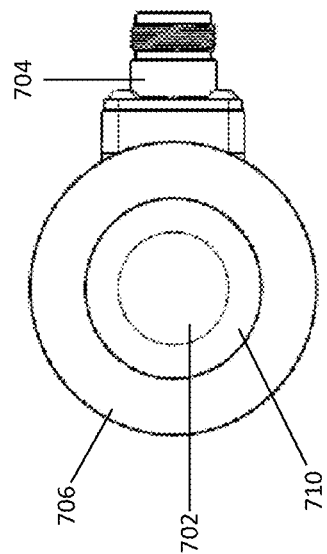
FIG. 7A is a front view of a third RF applicator and acoustic receiver sleeve configuration, according to an embodiment.
Figure 7C:
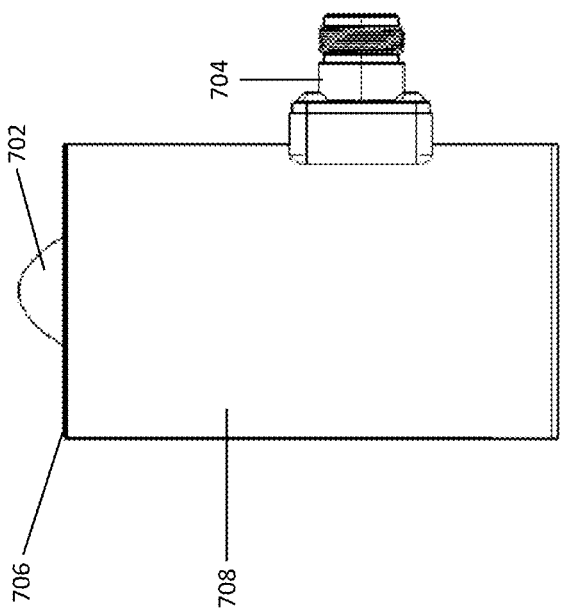
FIG. 7C is a side view of the third RF applicator and acoustic receiver sleeve configuration, according to an embodiment.

In another configuration, an acoustic receiver may have a conical shape and be positioned in an RF applicator, as shown in FIGS. 7A to 7D. FIG. 7A is a front view of a third RF applicator and acoustic receiver sleeve configuration embodiment. FIG. 7B is a perspective view of a third RF applicator and acoustic receiver sleeve configuration embodiment. Shown are open-ended hollow waveguide matching layer 706, open-ended hollow waveguide body 708, RF energy feed 704, insulation 710, and conical acoustic receiver 702 (with circular cross-section). FIG. 7C is a side view of a third RF applicator and acoustic receiver sleeve configuration embodiment. FIG. 7D is a top view of a third applicator and acoustic receiver sleeve configuration embodiment.

In another configuration, an acoustic receiver may have a rectangular shape and be positioned in an elliptical-shaped RF applicator, as shown in FIGS. 8A to 8D. FIG. 8A is a front view of a fourth RF applicator and acoustic receiver sleeve configuration embodiment. FIG. 8B is a perspective view of a fourth RF applicator and acoustic receiver sleeve configuration embodiment. Shown are open-ended hollow elliptical waveguide matching layer 806, open-ended hollow elliptical waveguide body 808, RF energy feed 804, insulation 810, and rectangular acoustic receiver 802 (with rectangular cross-section). FIG. 8C is a side view of a fourth RF applicator and acoustic receiver sleeve configuration embodiment. FIG. 8D is a top view of a fourth applicator and acoustic receiver sleeve configuration embodiment.

Figure 9B:
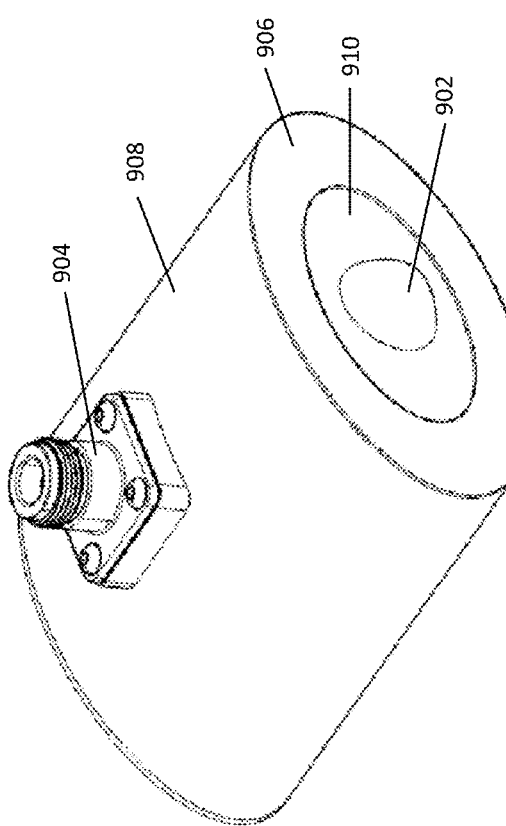
FIG. 9B is a perspective view of the fifth RF applicator and acoustic receiver sleeve configuration, according to an embodiment.
Figure 9D:
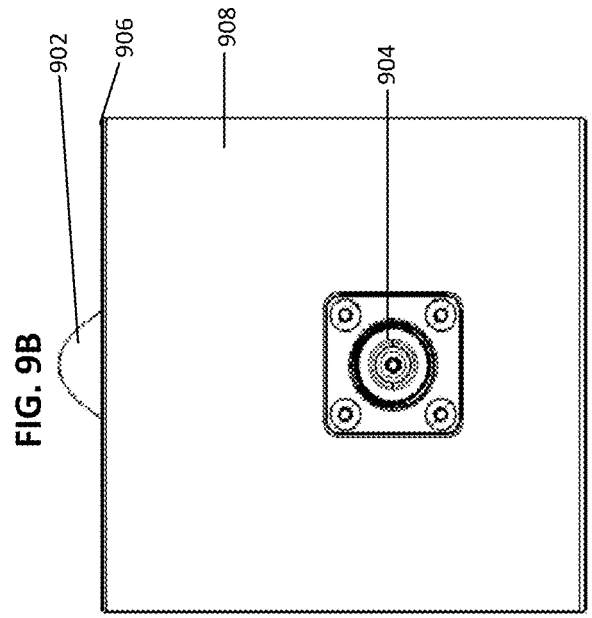
FIG. 9D is a top view of the fifth applicator and acoustic receiver sleeve configuration, according to an embodiment.
Figure 9A:
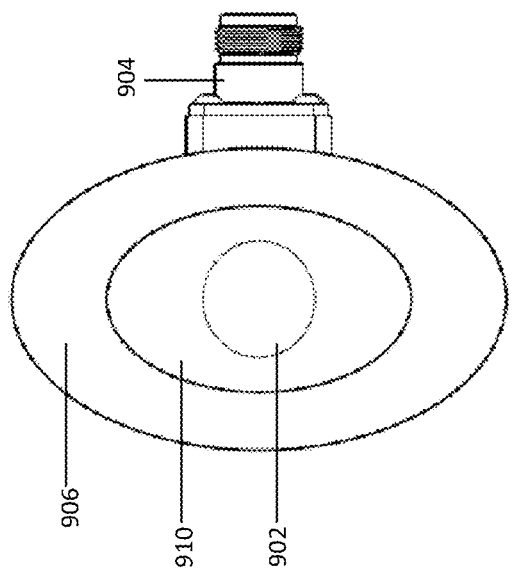
FIG. 9A is a front view of a fifth RF applicator and acoustic receiver sleeve configuration, according to an embodiment.
Figure 9C:
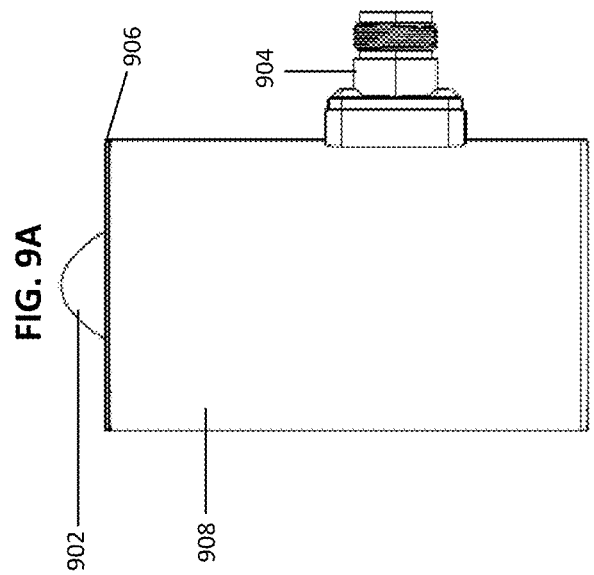
FIG. 9C is a side view of the fifth RF applicator and acoustic receiver sleeve configuration, according to an embodiment.

In another configuration, an acoustic receiver may have a conical shape and be positioned in an elliptical-shaped RF applicator, as shown in FIGS. 9A to 9D. FIG. 9A is a front view of a fifth RF applicator and acoustic receiver sleeve configuration embodiment. FIG. 9B is a perspective view of a fifth RF applicator and acoustic receiver sleeve configuration embodiment. Shown are open-ended hollow elliptical waveguide matching layer 906, open-ended hollow elliptical waveguide body 908, RF energy feed 904, insulation 910, and conical acoustic receiver 902 (with circular cross-section). FIG. 9C is a side view of a fifth RF applicator and acoustic receiver sleeve configuration embodiment. FIG. 9D is a top view of a fifth applicator and acoustic receiver sleeve configuration embodiment.

FIGS. 10A to 11D show a configuration having a circular acoustic receiver and a rectangular waveguide, as shown in FIGS. 6A to 6D. FIG. 10A is a perspective exploded view of a sixth RF applicator and acoustic receiver sleeve configuration, according to an embodiment. FIG. 10B is a side exploded view of the sixth RF applicator and acoustic receiver sleeve configuration, according to an embodiment. FIG. 10C is a top exploded view of the sixth RF applicator and acoustic receiver sleeve configuration, according to an embodiment. FIG. 10D is a side exploded view of the sixth RF applicator and acoustic receiver sleeve configuration, according to an embodiment.

A waveguide housing 1008 holds a ceramic 1016. A waveguide matching layer 1006 abuts the ceramic 1016 at a first end of the waveguide housing 1008. Acoustic isolation 1010 is positioned inside the waveguide housing 1008. An inner Faraday cage 1012 is positioned inside acoustic isolation 1010. The acoustic isolation 1010 may comprise cork, foam, or the like, and it may be affixed to the ceramic 1016. In some configurations (not shown), an air gap may be used. The inner Faraday cage 1012 is aligned with a thermoacoustic sensor 1002 having a seal 1014. Although the sensor 1002 is shown as having a rectangular shape and a seal 1014 configured for a rectangular-shaped sensor 1002, it is intended that this configuration may be adapted for other shapes of sensors. The waveguide housing 1008 is coupled to an RF energy feed 1004. A shielded connector 1018 for the inner Faraday cage 1012 is positioned at a second end of the waveguide housing 1008.

FIGS. 11A to 11D show the components of FIGS. 10A to 10D from an alternative view. FIG. 11A is an alternative perspective exploded view of the sixth RF applicator and acoustic receiver sleeve configuration, according to an embodiment. FIG. 11B is an alternative side exploded view of the sixth RF applicator and acoustic receiver sleeve configuration, according to an embodiment. FIG. 11C is an alternative top exploded view of the sixth RF applicator and acoustic receiver sleeve configuration, according to an embodiment. FIG. 11D is an alternative side exploded view of the sixth RF applicator and acoustic receiver sleeve configuration, according to an embodiment.

FIGS. 12A to 13D show a configuration having a circular acoustic receiver and a rectangular waveguide, as shown in FIGS. 6A to 6D. FIG. 12A is a perspective exploded view of a seventh RF applicator and acoustic receiver sleeve configuration, according to an embodiment. FIG. 12B is a side exploded view of the seventh RF applicator and acoustic receiver sleeve configuration, according to an embodiment. FIG. 12C is a top exploded view of the seventh RF applicator and acoustic receiver sleeve configuration, according to an embodiment. FIG. 12D is a side exploded view of the seventh RF applicator and acoustic receiver sleeve configuration, according to an embodiment.

A waveguide housing 1208 holds a ceramic 1216. Acoustic isolation 1210 is positioned inside the waveguide housing 1008. At an end of the acoustic isolation 1210 is a thermoacoustic sensor (without a lens) 1202. Although the sensor 1202 is shown as having a rectangular shape, it is intended that this configuration may be adapted for other shapes of sensors. Positioned on the sensor 1202 is a front, non-conductive seal 1214, a thin conductive layer 1220, an electromagnetic matching layer 1222, and an acoustic lens 1224. The waveguide housing 1208 is coupled to an RF energy feed 1204. A shielded connector 1218 and a back conductive seal 1226 are positioned at a second end of the waveguide housing 1208.

FIGS. 13A to 13D show the components of FIGS. 12A to 12D from an alternative view. FIG. 13A is an alternative perspective exploded view of the seventh RF applicator and acoustic receiver sleeve configuration, according to an embodiment. FIG. 13B is an alternative side exploded view of the seventh RF applicator and acoustic receiver sleeve configuration, according to an embodiment. FIG. 13C is an alternative top exploded view of the seventh RF applicator and acoustic receiver sleeve configuration, according to an embodiment. FIG. 13D is an alternative side exploded view of the seventh RF applicator and acoustic receiver sleeve configuration, according to an embodiment.

Figure 14:
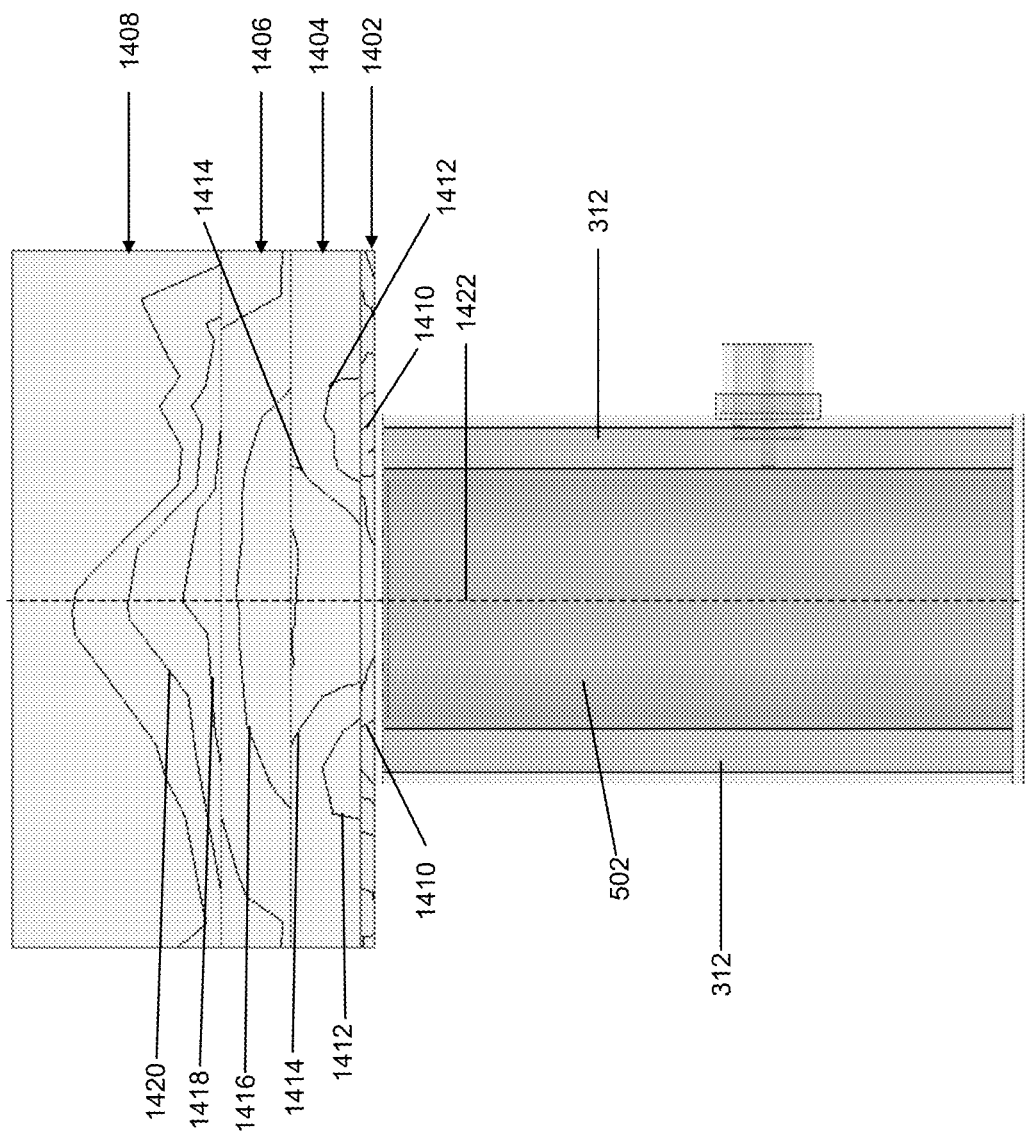
FIG. 14 is a contour map showing electric field strength in decibels in different tissue types for the RF applicator.

FIG. 14 is a contour map showing electric field strength in decibels in different tissue types for the open-ended hollow RF applicator 312. The electric field is shown exiting the open-ended hollow RF applicator 312 and traveling through a skin layer 1402, fat layer 1404, muscle layer 1406, and liver layer 1408. Contour line 1410 is 61 decibels, contour line 1412 is 53 decibels, contour line 1414 is 46 decibels, contour line 1416 is 23 decibels, contour line 1418 is 15 decibels, and contour line 1420 is 7 decibels. Peak electric field is shown near the open-ended hollow RF applicator 312 exit. As the electric field is dispersed through the tissue, the electric field becomes strongest near the thermoacoustic probe center axis 1422. Both contour line 1418 and contour line 1420 are located in the liver layer 1408 and are strongest near the thermoacoustic probe center axis 1422.

Figure 15:
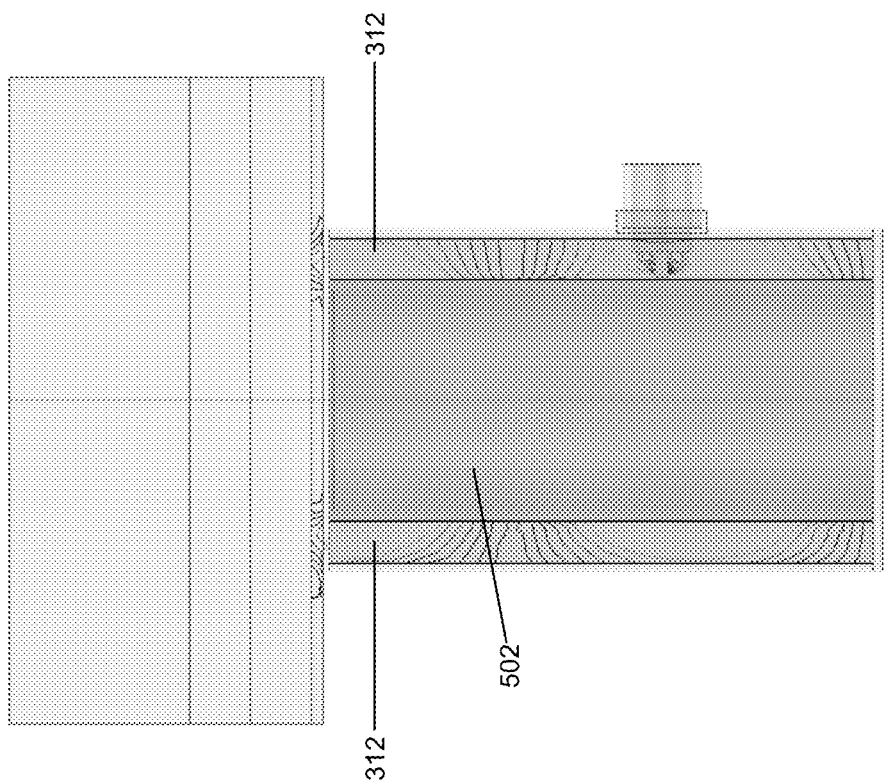
FIG. 15 shows electric field in the RF applicator in volts per meter.

FIG. 15 shows electric field in the RF applicator in volts per meter. The hollow cavity 502 has a very low electric field of less than 400 volts per meter. In contrast, the open-ended hollow RF applicator 312 has an electric field that is greater than 1600 volts per meter. The electric field that is generated in the open-ended hollow RF applicator 312 cancels itself in the hollow cavity 502 due to the symmetrical nature (sleeve shape) of the open-ended hollow RF applicator 312 surrounding the hollow cavity 502.

Figure 16:
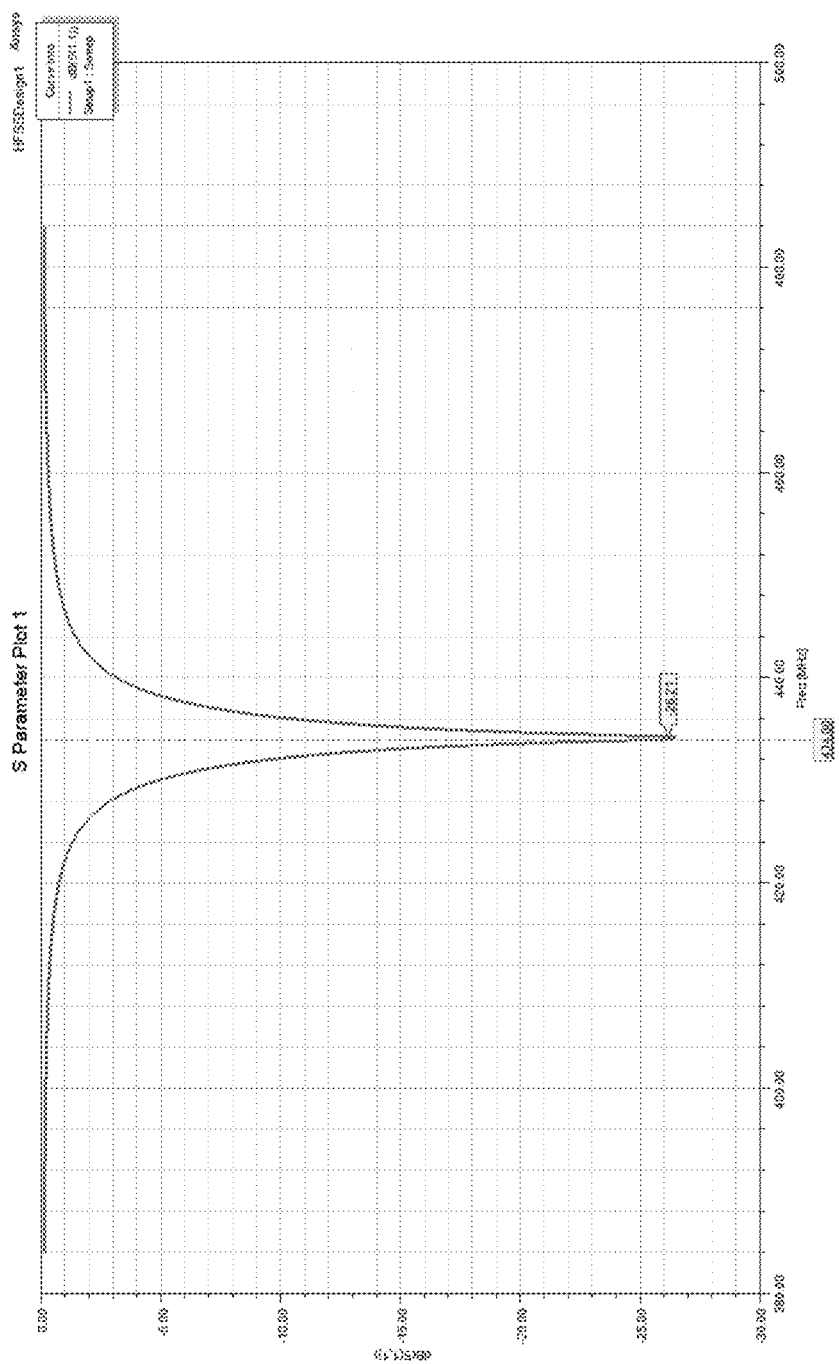
FIG. 16 shows reflected power in decibels at a target frequency for the RF applicator.

FIG. 16 shows reflected power in decibels at a target frequency for the open-ended hollow RF applicator 312. FIG. 16 shows the reflection coefficient at a 50 ohm reference impedance versus frequency for the open-ended hollow RF applicator 312. The reflection coefficient represents the amount of power that is transferred from a 50 ohm source into the open-ended hollow RF applicator 312 (i.e., reflected power). At 434 MHz, the design frequency of the open-ended hollow RF applicator 312, the reflection coefficient is −26 dB, which corresponds to 99.75% of the power from a 50 ohm source being transferred to the open-ended hollow RF applicator 312.

Although embodiments have been described above with reference to the accompanying drawings, those of skill in the art will appreciate that variations and modifications may be made without departing from the scope thereof as defined by the appended claims.

What is claimed is:

1. A thermoacoustic measurement probe comprising:
   an open-ended hollow radio-frequency (RF) waveguide; and
   a thermoacoustic transducer;
   wherein the open-ended hollow RF waveguide, in the form of a sleeve, surrounds and is mechanically joined to the thermoacoustic transducer.

2. The thermoacoustic measurement probe of claim 1, wherein the thermoacoustic transducer and open-ended hollow RF waveguide form a circular cross-sectional shape.

3. The thermoacoustic measurement probe of claim 1, wherein the thermoacoustic transducer and open-ended hollow RF waveguide form an elliptical cross-sectional shape.

4. The thermoacoustic measurement probe of claim 1, wherein the thermoacoustic transducer and open-ended hollow RF waveguide form a rectangular cross-sectional shape.

5. The thermoacoustic measurement probe of claim 1, wherein a sensor of the thermoacoustic transducer has a circular cross-sectional shape.

6. The thermoacoustic measurement probe of claim 1, wherein a sensor of the thermoacoustic transducer has an elliptical cross-sectional shape.

7. The thermoacoustic measurement probe of claim 1, wherein a sensor of the thermoacoustic transducer has a rectangular cross-sectional shape.

8. The thermoacoustic measurement probe of claim 1, wherein an end of a sensor of the thermoacoustic transducer has a conical shape.

9. A thermoacoustic measurement probe comprising:
   a radio-frequency (RF) waveguide having a cavity; and
   a thermoacoustic transducer positioned in the cavity of the RF waveguide.

10. The thermoacoustic measurement probe of claim 9, wherein the cavity of the RF waveguide has a circular cross-sectional shape.

11. The thermoacoustic measurement probe of claim 9, wherein the cavity of the RF waveguide has an elliptical cross-sectional shape.

12. The thermoacoustic measurement probe of claim 9, wherein the cavity of the RF waveguide has a rectangular cross-sectional shape.

13. The thermoacoustic measurement probe of claim 9, wherein a sensor of the thermoacoustic transducer has a circular cross-sectional shape.

14. The thermoacoustic measurement probe of claim 9, wherein a sensor of the thermoacoustic transducer has an elliptical cross-sectional shape.

15. The thermoacoustic measurement probe of claim 9, wherein a sensor of the thermoacoustic transducer has a rectangular cross-sectional shape.

16. The thermoacoustic measurement probe of claim 9, wherein an end of a sensor of the thermoacoustic transducer has a conical shape.

17. The thermoacoustic measurement probe of claim 9, wherein a ceramic is positioned in the cavity.

18. The thermoacoustic measurement probe of claim 17, wherein an acoustic isolation is positioned in the ceramic.

19. The thermoacoustic measurement probe of claim 9, further comprising an RF feed coupled to the RF waveguide, and a connector coupled to the thermoacoustic transducer via an opening in the RF waveguide.

20. A thermoacoustic measurement probe comprising:
   a cylindrical radio-frequency (RF) waveguide housing;
   a cylindrical ceramic inside the cylindrical RF waveguide housing;
   a cylindrical acoustic isolation inside of the cylindrical ceramic; and
   a thermoacoustic sensor at an end of the cylindrical acoustic isolation.

* * * * *